United States Patent [19]

Crostack

[11] Patent Number: 4,459,851
[45] Date of Patent: Jul. 17, 1984

[54] METHOD AND DEVICE FOR THE LOCALIZATION AND ANALYSIS OF SOUND EMISSIONS

[76] Inventor: Horst A. Crostack, Beringweg 2, 5860 Iserlohn, Fed. Rep. of Germany

[21] Appl. No.: 380,731
[22] PCT Filed: Sep. 5, 1981
[86] PCT No.: PCT/DE81/00137
 § 371 Date: May 7, 1982
 § 102(e) Date: May 7, 1982
[87] PCT Pub. No.: WO82/00893
 PCT Pub. Date: Mar. 18, 1982

[30] Foreign Application Priority Data

Sep. 10, 1980 [DE] Fed. Rep. of Germany ....... 3033990
Sep. 10, 1980 [DE] Fed. Rep. of Germany ... 8024132[U]

[51] Int. Cl.³ ............................................ G01N 29/04
[52] U.S. Cl. ..................................................... 73/587
[58] Field of Search ......................... 73/587, 658, 597;
                                                   367/99; 235/400

[56] References Cited

U.S. PATENT DOCUMENTS

| | | | |
|---|---|---|---|
| 3,875,381 | 4/1975 | Wingfield et al. | 73/587 |
| 4,004,463 | 2/1977 | Vercellotti et al. | 73/587 |
| 4,033,179 | 7/1977 | Romrell | 73/587 |
| 4,354,388 | 10/1982 | Diepers et al. | 73/628 |

FOREIGN PATENT DOCUMENTS 1516601 9/1977 Fed. Rep. of Germany.
7406207 9/1975 France.
7607130 10/1976 France.

OTHER PUBLICATIONS

The Soviet Journal of Non-Destructive Testing, vol. 16, Aug. 1980, No. 8, New York, U.S.A.

*Primary Examiner*—Anthony V. Ciarlante
*Attorney, Agent, or Firm*—Toren, McGeady and Stanger

[57] ABSTRACT

A method for localizing and analyzing sound emissions, wherein the position of the sound emission source is determined by incoming sound pulses at various measuring locations. The arrival time of a pulse or of a pulse characteristic is measured in three or more adjacent portions of each measuring location whose width is smaller than the expected sound field diameter. From this, the propagation time difference for the portion of each measuring location is determined and the sound arrival direction is determined from these propagation time difference values for each measuring location. Subsequently, the position of the sound emission source is determined from these direction values and the position coordinates of the measuring locations.

The device for carrying out this method has three or more separate converter elements (1) for each receiver measurement head (E) whose total width is smaller than the expected sound field diameter.

7 Claims, 1 Drawing Figure

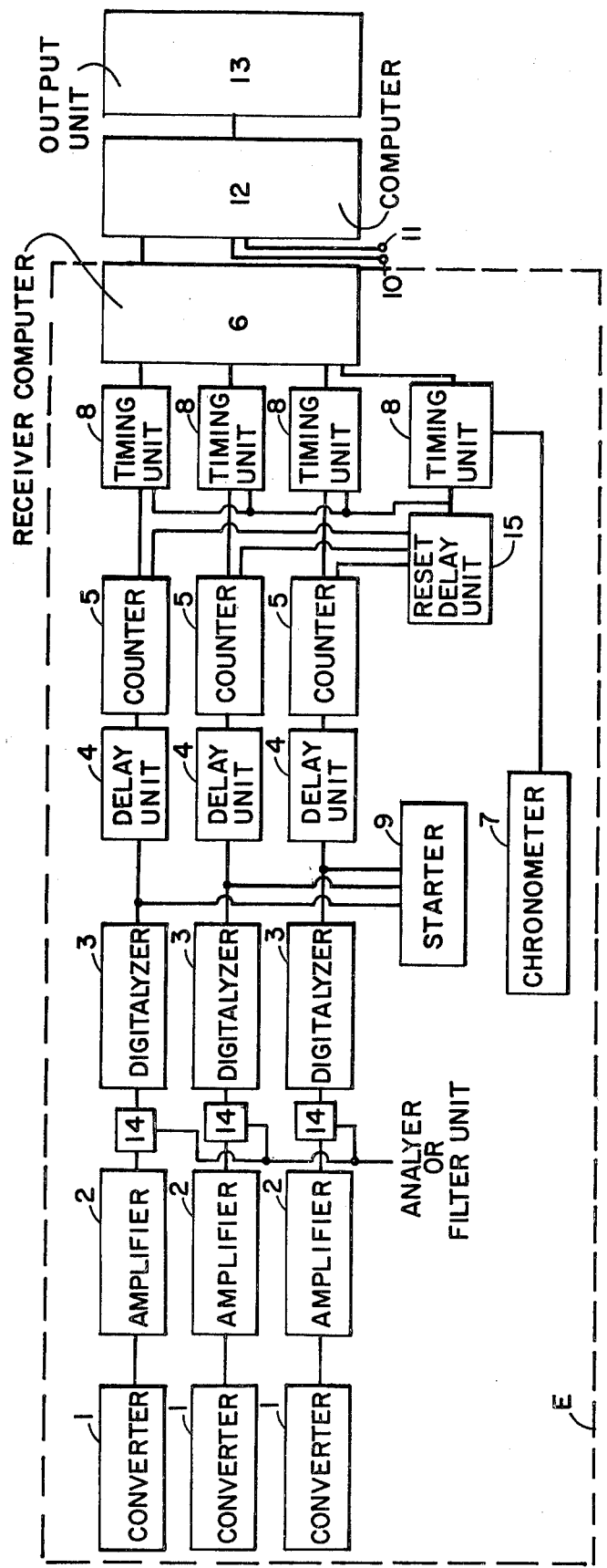

METHOD AND DEVICE FOR THE LOCALIZATION AND ANALYSIS OF SOUND EMISSIONS

The invention relates to a method for localizing and analyzing sound emissions, wherein the position of the sound-emitting source is determined by incoming sound pulses at various measuring locations. Further, the invention relates to a device operating in accordance with this method for localizing and analyzing sound emissions, which is particularly intended for testing for points of damage in apparatus and structural components, and for monitoring apparatus and structural components.

The object of the invention shall be explained below with reference to the principal field of application of the invention. However, the invention cannot only be used in this field, but in any other field in which a localization of the source of sound emissions by incoming sound pulses is to be effected.

In the operation of machines and apparatus, noises may occur which are produced in the interior of the materials and are related to an impending failure. For example, cracks in the microrange which are in the process of formation emit such sound waves, sometimes a long time prior to the failure. These sound waves are utilized for an early recognition of damage, so that the degree of damage and the continuance of the failure can be detected. In addition to the analysis of the processes, i.e. definition of the type of sound sources, particularly the localization of the sound source is of substantial importance for finding remedy measures.

As is well known, sound sources are localized by measuring the differences in propagation time which occur in the travel of the sound from the sound source to various receivers which are arranged individually and in large spacings around the source, and by computing the position of the sound source from these differences in propagation time with the aid of the position coordinates of the receivers. When this method is used for points of damage which are already existing or in the process of formation, several receivers are fastened to the surface of the sample in spacings of 1 to 5 m. When a sound pulse reaches the receivers, the signals emitted by these receivers start a counting of the propagation time. The propagation times of the adjacent probes are compared and the position of the sound source is determined from the differences in propagation time and from the coodinates of the receivers. (H. Bretfeld, A. Möller und H. -A. Crostack: Anwendung der Schallemissionanalyse bei der Belastung eines Druckbehälters mit pulsierendem Innendruck; Materialprüfung [Utilization of the Sound Emission Analysis in Stressing a Pressure Container with Pulsating Internal Pressure; Material Testing] 19 (1977) 11, Pages 467/70).

The following essential prerequisites must be met in order to obtain correct results in this known determination of the position:

1. The velocity developed by the sound wave on its travel from the sound source to the receiver must be known, because otherwise it would not be possible to compute from the propagation time values the distance travelled by the sound wave and, thus, the distance of the sound source from the receiver.

2. The sound pulses may not occur in a dense time sequence, but must have distinct spacings. An erroneous localization results when a new pulse occurs at a different point before the wave of the first pulse has reached all the receivers required for the localization. (H.-D. Steffens und H.-A. Crostack: Einflussgrössen bei der Analyse von Schallemissionen; Zeitschrift für Werkstofftechnik [Influence Variables in the Analysis of Sound Emissions; Magazine for Material Engineering] (1973), 8, Pages 442/7).

3. The sound pulses must be very similar to one another because a change in the type of waves or in the pulse shape (for example, the amplitude or the rise time) causes the electronic recording instruments (triggers) to respond at different times (H. D. Steffens, D. Krempel, D. Stegemann und H.-A. Crostack: Analyse von Signalen der Schallemission; Zeitschrift für Werkstofftechnik [Analysis of Signals of Sound Emissions; Magazine for Material Engineering] 6 (1975) 3, Pages 88/94).

To ensure that "critical" sources are localized, and not the sources of disturbing noises, the sound source must be identified. For this purpose, an analysis is required which, in the known methods and the devices operating in accordance with the methods, can only be carried out parallel to the localization, but not simultaneously with the localization.

In the case of the sound pulses to be localized which are produced by sound emission events, none of the abovementioned conditions can be met, as shall be explained in the following with reference to the numbers used above.

Concerning number 1: Sound Velocity:

When a single sound emission event occurs, usually in the manner of a pulse, longitudinal and transverse waves are released which, in addition, have an angle-dependent intensity (beam characteristic). As a result, these waves have different intensities depending upon the event, and they propagate with different velocities.

When these waves pass through a solid body (apparatus, machine), they are reflected, damped and converted. In addition to the pure mode conversion, guided waves may also be generated (surface waves, waves in plates, pipes, rods, etc.) which sometime have a very high dispersion. However, this means that the velocity of propagation becomes dependent on unknown variables, i.e., the frequency spectrum. Since, in addition, this conversion depends upon the propagation path as a function of the geometry of the body, a different average velocity exists for each distance between sound source and receiver.

In the known localization methods and the devices operating in accordance with these methods, the velocity is given as constant, contrary to the actual conditions. This leads to substantial deviations of the result from the real conditions.

A similar situation exists if the sound passes through different media with different velocities, for example, through a water-filled container. Also in this case, giving a constant velocity leads to errors in the evaluation of the measurement results. Therefore, it has not been considered useful in the past to utilize the sound emission method for testing purposes.

Concerning number 2: Chronological Spacing of the Sound Pulses:

The condition that sound pulses occur far enough apart with respect to time can only be met in individual cases, for example, in a pressure test with controllable stress conditions. In the case of events which follow one another very densely spaced with respect to time, such as, for example, plastic deformation, phase transitions in the structure or manufacturing noises, as they occur in welding and soldering processes, a localization had been impossible in the past.

Concerning number 3: Similarity of the Pulses:

This third requirement cannot be met at all in real structures (H.-D. Steffens, D. Stegemann, D. Krappel und H.-A. Crostack: [Analyse von Signalen der Schallemission; Zeitschrift für Werkstofftechnik (Analysis of Signals of Sound Emissions: Magazine for Material Engineering] 6 (1975) 3, Pages 88/94). The sound source emits longitudinal and transverse waves whose intensities vary in dependence upon the direction. The relative intensity conditions are further changed as a result of the propagation and the wave conversion mentioned under number 1 and the generation of guided waves. Since, in addition, the spectra are changed by the damping and the receivers are designed for certain resonant frequencies, it may happen that the electronics of one receiver responds to the longitudinal wave portions of the pulse, and that of another receiver responds to the transverse portions (or, for example, surface waves). This leads to substantial errors in the localization, and the allocation of the sound source is not possible.

For these reasons, it is very difficult to determine the position of sound sources by means of the known methods, even in simple structural components, such as plates or pipes. In the case of complicated geometries as they exist in machines and apparatus, these difficulties become so great that a localization is impossible.

It is the object of the invention to provide a method and a device which make it possible to perform a localization (determination of position of formation) in a simple manner, even when the propagation velocity of the pulse is not known, when the sequence of signals is very dense with respect to time, when the signals are very noisy, when the pulses are substantially changed over long travel paths, and when the geometries of the structural components are complicated, and thereby to expand substantially the field of application of the sound emission method in the testing for points of damage.

The invention resides in that the pulse arrival time is measured in three or more closely adjacent portions of each measurement point, the widths of these portions being smaller than the expected sound field diameter, that the propagation time differences for the portions of each measurement point are determined from the pulse arrival times directly or after a real time analysis, and that the direction in which the sound emission source is located is determined from these propagation time difference values for each measurement point, and that, subsequently, the position of the sound emission source is determined from the direction values and the position coordinates of the measurement points.

Further, the invention resides in a device for carrying out this method, wherein each receiver measurement head has three or more separate transformer elements whose total width is smaller than the expected sound field diameter.

Additional features of the invention are subject matter of the subclaims.

An embodiment representing an example of a device for carrying out the method in accordance with the invention is described in the following with the aid of the block diagram of such a device illustrated in the drawing. For simplicity's sake, only one of the receiver measurement heads of the device is illustrated and described, since the measurement heads are the same in their principal design and manner of operation.

In the illustrated embodiment, the receiver E is composed of three individual sound converter elements 1. However, it is also possible to combine more converter elements 1 in a measurement head E if their total width does not exceed the desired maximum limit. The diameter of the receiver E is small as compared to the size of the expected sound field, i.e., for example, smaller than 25 mm, so that the elements 1 are located within a sound field range of the source, for example, within the 6 dB-response down in the case of zigzag-waves. The elements 1 may consist of any chosen converter materials and structures (piezoelectrical, electrodynamical, acousto-optical, magnetostrictive, or the like).

To each converter element 1 there is connected, in the following sequence, an amplifier and impedance transformer 2, a digitalizer 3, a delay unit 4, a counter 5 and a timing unit 8. The digitalizers 3 are at their outputs additionally connected to a counter starter 9 which serves to simultaneously switch on all counters 5; the starter 9 is switched by the first arriving digitalized pulse, so that it starts all counters 5. The delay time of the delay units 4 is the same for all channels of a receiver E, for example, 20 ns. The counters 5 are stopped by the first pulse which arrives with the predetermined delay over the receiver channel assigned to it. A chronometer 7 serves to measure the absolute time at the start of the counter 5. This chronometer 7 as well as the counters 5 are connected with their signal outputs to the inputs of a microprocessor 6 into which the measured values of the counters 5 and of the chronometer 7 are fed controlled by the timing unit 8. Such a separate computer 6 is provided for each receiver E. The computer 6 determines from the entered propagation time values the propagation time differences between the individual elements 1 of a receiver and, therefrom, computes the direction from which the pulse has arrived, and, parallel thereto, stores the absolute time at the counter start as a characteristic value for the pulse and, subsequently, resets the counters 5 with a delay by a reset delay unit 15 connected to the timing units 8 and the counters 5. Further, a filter or analyzer unit 14 can be located between each amplifier 2 and digitalizer 3.

All microprocessors 6 of a device are connected with their outputs to a computer 12 of the device. In the drawing, reference numerals 10 and 11 designate lines through which the characteristic values of other receivers are fed into the computer 12. The output unit 13 is connected in series to the computer 12. It is possible to connect filters or analyzing units (not shown) between the impedance transformers 2 and the digitalizers 3 which can separate the characteristics from a noisy signal.

The device operates as follows:

After the occurrence of a sound event whose source is to be localized, the emitted sound pulse arrives at the elements 1 after different propagation times depending upon the different position coordinates of the elements 1. From these pulses, these elements 1 produce electric signals which are amplified in the amplifiers 2 of each element 1, possibly with a prior or subsequent analysis and filtering 14, and are subsequently digitalized in the digitalizers 3. The digitalized signals derived from the converter signals or, when an analyzing unit or a filter is arranged intermediately, the digitalized signals derived from their analyzed values, are supplied to the counterstarter 9 as well as to the delay unit 4. The first arriving signal has the effect that the counterstarter 9 simultaneously starts all counters 5 of the receiver E assigned to it. This first signal reaches the counter 5 through the delay unit or only after the delay time and switches it off. The signals of the other channels of the receiver arriving later reach their counters 5 also only after the delay time and additionally after the propagation time difference relative to the channel in which the first signal had arrived. In accordance therewith, the other counters 5 are switched off later, so that the differences of the counter values of the channels of a receiver correspond to the propagation time differences. The time at the counter start had been measured by means of the chronometer 7 parallel to the counting of the propagation time differences.

After all counters 5 of a receiver E have been stopped, its values, controlled by the timing unit 8, are fed into the processing computer 6. For this purpose, the absolute time measured by the chronometer 7 at the start of the counter 5 is stored as the characteristic value for the pulse. The counters 5 of the receiver E assigned to the computer 6 are reset with a delay after the value for the absolute time has been transferred to the processing computer 6. Each computer 6 computes for the receiver E assigned to it the propagation time differences between the arrivals of the pulses or characteristics at the individual converter elements 1 and the resulting direction from which the pulse has been arriving at the receiver E.

The direction values of the microprocessors 6 of all receivers E are fed into the computer 12 of the device, into which the coordinates of the receivers E had been fed beforehand. In a subsequent computing step, the computer 12 now relates these coordinates to the direction values and, subsequently, defines the point of intersection of the direction lines as the location of the sound source by superimposing the directions.

In the above-explained analysis of the individual elements prior to digitalization, the arrival of a certain characteristic of the sound pulse is measured. Instead, it is possible to perform an analysis (for example, frequency analysis) correlated directly to the direction, parallel to the determination of the direction.

The directions of the receivers can also be stored and correlated to one another at a later time, which makes possible the processing of signals in very rapid succession. While in the known methods it was possible to process successions of about 100/sec. (depending on the spacing of the receivers), it is now possible to process independently from this spacing and successions of maximum values of about 1-2 Mio/sec.

Further essential advantages over the state of the art reside in that the determination becomes independent from the velocity of the pulse from the source to the receiver because the direction of the sound pulse is determined within the individual elements 1;

the pulses within the individual elements 1 (spacing of elements < sound field diameter) remain similar, so that the type of wave on which the respective receiver takes a preferred bearing becomes unimportant and the resulting error is eliminated;

since the direction of the pulse is determined for each receiver, it is no longer necessary to wait until the pulse has reached all the receivers required for the localization. The values of the individual receivers can be stored;

since the pulses remain similar within the individual elements 1, an analysis can be performed easily in real time which is directly correlated to the direction of the pulse which is also immediately determined, or the direction is determined from their characteristics. In this manner, an unequivocal characterization of the pulse becomes possible, without having to take into consideration the usual propagation time differences;

even complicated geometries can be tested because the directions are determined immediately for each receiver. By means of the direction determination, reflections and mode conversions can be easily taken into consideration and do not falsify the measurement result.

I claim:

1. Method for localizing and analyzing sound emissions in the testing of an article of apparatus or structural components for points of damage, wherein the location of the sound emission source is determined from the imcoming sound pulse at a plurality of individual measuring receivers in spaced arrangement on the surface of the article being tested, characterized therein by dividing each measuring receiver into at least three separate sound converter elements (1) having a total width smaller than the expected sound field diameter, measuring the arrival time of a pulse or of a pulse characteristic in each of said elements (1), determining the propagation time difference for said elements (1) of each measuring receiver (E), determining the sound arrival direction from these propagation time differences for each measuring receiver (E), and, subsequently, determining the position of the sound emission source from the direction values and the position coordinates of said measuring receivers (E).

2. Method according to claim 1, characterized in by performing a sound analysis, for example, a frequency analysis, at the individual measuring receivers (E) parallel to the determination of direction which analysis is directly correlated to the direction.

3. Method according to claim 1, characterized by analysing or filtering of the signals of the individual elements (1) prior to digitalizing the signals.

4. Device for localizing and analyzing sound emissions in the testing of an article of apparatus or structural components for points of damage, comprising a plurality of measurement receivers (E) to be mounted in spaced relation on the surface of the article to be tested, said measurement receivers (E) including converter elements (1) converting the received sound pulses to electric signals, wherein the improvement comprises that each said receiver (E) includes at least three separate converter elements (1) having a total width smaller than the expected sound field diameter, an amplifier (2), a digitalizer (3) and a counter (5) connected in series to each said converter element (1), a timing unit (8) connected in series to each said counter (5), processor computer means (6,12) are connected in series to said counters (5) via said timing units (8) for determining the propagation time differences between the sound pluses received by the individual said converters (1) of each said receiver (E) and for evaluating the differences of each said receiver (E) for determining the direction in which the sound emission source is located in relation to each said receiver (E) and for the correlation of the directions with the receiver coordinates for localizing the sound emission source.

5. Device according to claim 4, characterized in that said processor computer means (6, 2) comprise a microprocessor (6) for each said receiver (E) connected in series to each of said counters (5) of said receivers (E) for receiving the counter values and for evaluating the counter values for the purpose of determining the direction in which the sound emission source is located relative to said receiver (E), and a computer (12) connected in series to each of said microprocessors (6) for the localization of the sound emission source from the supply direction values of said receiver computers (6) and the receiver coordinates by determining the point of intersection of the directions.

6. Device according to claim 4 or 5, characterized by a counter starter (9) interconnected with said digitalizers (3) of each receiver (E) for simultaneously starting all said counters (5) of said receiver (E) when the first pulse arrives, by a separate unit (4) connected in series to each said digitalizer (3) of said receiver (E) between said digitalizer (3) and the series connected said counter (5) with said counter being stopped by the arrival of the pulse, said delay units (4) having the same delay time for all series connected elements of said receiver (E), and by a chronometer (7) for each said receiver (E) for measuring the time of the counter start, the values of said chronometer (7) being fed to said microprocessor (6) of the assigned said receiver (E) via said timing unit (8).

7. Device according to claim 4 or 5, characterized in that an analysis unit (14) is connected in series between each said amplifier (2) and the series connected said digitalizer (3) of each said converter element (1).

* * * * *